United States Patent [19]

Hillman

[11] 4,133,875

[45] Jan. 9, 1979

[54] METHOD OF CONTROLLING DENTAL CARIES WITH STREPTOCOCCUS MUTANS MUTANT STRAINS

[75] Inventor: Jeffrey D. Hillman, Jamaica Plain, Mass.

[73] Assignee: Forsyth Dental Infirmary for Children, Boston, Mass.

[21] Appl. No.: 880,499

[22] Filed: Feb. 23, 1978

[51] Int. Cl.$^2$ .................... A61K 37/00; A61K 7/16
[52] U.S. Cl. .................................... 424/93; 424/50
[58] Field of Search .................................. 424/50, 93

[56] References Cited

PUBLICATIONS

Klein et al.–Chem. Abst., vol. 83 (1975), p. 41054c.
Freedman et al.–Chem. Abst., vol. 81, (1974), p. 118325k.

Primary Examiner—Sam Rosen
Attorney, Agent, or Firm—Richard P. Crowley

[57] ABSTRACT

Mutant strains have been isolated from *Streptococcus mutans* strain BHT-2(str) which are characterized by a single point mutation in the structural gene for the enzyme, L(+) lactate dehydrogenase, this enzyme being normally responsible for lactic acid production by this bacterium. *Streptococcus mutans* is believed to be a principal pathogen in dental caries, a disease characterized by the dissolution of the mineral portion of the tooth caused by acid resulting from the interaction of bacteria on the tooth surface with carbohydrates. The mutant strains of the invention will be found useful as prototype nonvirulent effector strains in controlling the incidence and severity of dental caries.

11 Claims, No Drawings

METHOD OF CONTROLLING DENTAL CARIES WITH STREPTOCOCCUS MUTANS MUTANT STRAINS

BASIS OF WORK

The invention described and claimed in this application has been developed in whole or in part under NIDR Grant No. DE04529 of the National Institute of Health, Department of Health, Education and Welfare.

BACKGROUND OF THE INVENTION (1) Field of the Invention

This invention relates to certain mutant strains of *Streptococcus mutans* strain BHT-2(str), their mutagenesis and isolation from the parent strain, and their use as an effector strain in the replacement therapy of dental caries.

(2) Description of the Prior Art

Dental clinical investigators have long wrestled with the problem of preventing, or at least alleviating, dental caries, a disease characterized by the dissolution of the mineral portion of the tooth. If permitted to go unchecked, the disease ultimately attacks and penetrates the pulp chamber of the tooth, resulting in pain and loss of viability of the tooth which may necessitate costly repair of the tooth, or even extraction.

A clean tooth will not decay; however, it is also virtually impossible to keep one's teeth continuously clean. And despite the most vigorous cleaning regimen, carious lesions do occur.

Over the years, various methods have been developed and tried, with varying results, to prevent, or at least alleviate, the problem of dental caries. The application of alkali metal or tin flourides to the teeth topically, in drinking water, and in dentifrice preparations containing these flouride compounds which release flouride ions in water is known to be somewhat beneficial. However, it has also been discovered that these compounds tend to lose their effectiveness upon aging. Moreover, flouride reduces caries at best by only about 20% when used in toothpaste.

It has also been proposed to prevent dental caries by coating the tooth surfaces with various polymeric materials. However, at least one of these proposals suffers from at least two drawbacks. The teeth must first be etched with phosphoric acid; and, the treatment has been found to be effective only in young children who have not yet developed dental caries.

The formation of carious lesions in teeth, it has been observed, is apparently caused by acids produced by bacteria, e.g. the interaction between carbohydrates, notably sucrose, and bacteria on the tooth surfaces, as an end product of their metabolism. A variety of specific organisms have been described as etiologic agents of dental caries, notable among which are bacteria of the genus Streptococcus. Various Streptococci have been isolated from the oral cavity and have been linked to the formation of dental caries in experimental animals.

Antibiotics such as penicillin have been suggested for reducing caries, and dentifrices containing penicillin have been tested and found to be effective. However, the antibiotics are not selective in the destruction of oral bacteria and destroy both the useful and harmful bacteria in the mouth indescriminately, resulting in microbial imbalance in the mouth which can have serious consequences.

A number of vaccines have been proposed for immunization against dental caries in animals. Various of these proposals are summarized in U.S. Pat. No. 3,879,545 issued to Gaffar and Kestenbaum for "Vaccines for the Prevention of Dental Caries", issued on Apr. 22, 1972. As disclosed therein, the active ingredient of the vaccine is a polyfructan (or levan) polysaccharide produced by elaboration of certain strains of Streptococcus, particularly Streptococcus strain SS2.

There are also disclosed in U.S. Pat. Nos. 3,931,398 and 3,993,747, methods of immunization against dental caries employing as the active ingredient the polysaccharide of U.S. Pat. No. 3,879,545, or the polyglucan elaboration product described therein from *Streptococcus mutans*, or the enzyme involved in the synthesis of these polysaccharides selected from among levansucrase (fructosyl transferase) and dextransucrase (glucosyl transferase).

A large body of evidence has implicated *Streptococcus mutans* as a principal pathogen in dental caries of both rodents and humans. Fitzgerald, R. J. and P. H. Keyes. 1960. Demonstration of the Etiologic Role of Streptococci in Experimental Caries in the Hamster. *J. Am. Dent. Ass.* 61: 9–13; Gibbons, R. J., K. S. Berman, K. S. Knoetter, and B. Kapsimalis. 1966. Dental Caries and Alveolar Bone Loss in Gnotobiotic Rats Infected With Capsule Forming Streptococci of Human Origin. *Archs. oral Biol.* 11: 549–559; Krasse, B. 1966. Human Streptococci and Experimental Caries in Hamsters. *Archs. oral Biol.* 11: 429–436; and Zinner, D. D., J. M. Jablon, A. P. Aron, and M. S. Saslaw. 1965. Experimental Caries Induced in Animals by Streptococci of Human Origin. *Proc. Soc. Exp. Biol.* 11: 429–436; deStoppelaar, J. D., J. van Houte, and O. Backer Dirks. 1969. The Relationship Between Extracellular Polysaccharide Producing Streptococci and Smooth Surface Caries in 13-year-old Children. *Caries Res.* 3: 190–199; Krasse, B., H. V. Jordan, S. Edwardsson, I. Svensson, and L. Trell. 1968. The Occurrence of Certain "Caries Inducing" Streptococci in Human Dental Plaque Material. *Archs. oral Biol.* 13: 911–918; and Littleton, N. W., S. Kakehashi, and R. J. Fitzgerald. 1970. Recovery of Specific "Caries-Inducing" Streptococci From Carious Lesions in The Teeth of Children. *Archs. oral Biol.* 15: 461–463.

The characteristic features of *Streptococcus mutans* which appear likely to account for its cariogenic potential include not only its ability to accumulate on tooth enamel, but also its ability to produce, via fermentative processes, large amounts of lactic acid. Gibbons, R. J. and R. J. Fitzgerald. 1969. Dextran-induced agglutination of *Streptococcus mutans* and its potential role in the formation of microbial dental plaques. *J. Bacteriol.* 98: 341–346; Makinen, K. K. 1972. The role of sucrose and other sugars in the development of dental caries: a review. *Int. Dent. J.* 22: 362–386; Drucker, D. B. and T. H. Melville. 1968. Fermentation end-products of cariogenic and non-cariogenic Streptococci. *Archs. oral Biol.* 13: 563–570; Jordan, H. V. 1965. Bacteriological aspects of experimental dental caries. *Ann. N.Y. Acad. Sci.* 131: 905–912; and Tanzer, J. M., M. I. Krichevsky, and P. H. Keyes. 1969. The metabolic fate of glucose catabolized by a washed stationary phase caries-conducive Streptococcus. *Caries Res.* 3: 167–177.

In recent years, considerable success has been achieved in preventing and controlling certain bacterial infections by purposefully colonizing susceptible host tissues with non-virulent analogs of disease-causing microorganisms. Davidson, J. N. and D. C. Hirsh. 1976.

Bacterial Competition as a Means of Preventing Neonatal Diarrhea in Pigs. *Infect. Immun.* 13: 1773–1774; Shinefield, H. R., J. C. Ribble, and M. Boris. 1971. Bacterial Interference Between Strains of *Staphylococcus aureus*, 1960–1970. *Amer. J. Dis. Child.* 121: 148–152. The basis of this phenomenon, termed bacterial interference, is in no single case completely understood, but in general terms appears to involve a competitive and/or antibiotic action of the non-virulent strain, the so-called effector strain, on its pathogenic counterpart. Thus, for an organism to serve as an effector strain in the replacement therapy of a bacterial infection, it must be (a) non-virulent itself, and (b) able to compete successfully with its pathogenic counterpart.

SUMMARY OF THE INVENTION

Mutant strains have been isolated from *Streptococcus mutans* strain BHT-2(str) following mutagenesis and plating on glucose tetrazolium medium characterized by a single point mutation in the structural gene for the enzyme, L(+) lactate dehydrogenase (LDH); gram positive, spheroidal cells occurring in pairs and chains; and by bright red colonies relatively larger in size than colonies of the parent strain on glucose tetrazolium medium.

The mutant strains, according to the invention, when compared to the parent strain, in the case of resting cell suspensions, produces less total titratable acid when incubated in the presence of glucose; make no detectable lactic acid when incubated in the presence of glucose in the case of resting and growing cultures; adhere better to hydroxyapitite; and accumulate more plaque when grown in the presence of sucrose.

Quite advantageously, the characteristics of the isolated mutant strain provide a useful effector strain for the prevention and alleviation of dental caries in animals.

Two cultures, typical of the mutant strains of the invention which have been isolated, have been deposited with the American Type Culture Collection, 12301 Parklawn Drive, Rockville, Md. 20852, and are identified by deposit numbers ATCC31341 and ATCC 31377; these cultures are further identified as *Streptococcus mutans* JH140; and *Streptococcus mutans* JH145.

DETAILED DESCRIPTION AND PREFERRED EMBODIMENTS OF THE INVENTION
ORGANISMS AND MEDIA

*Streptococcus mutans* strain BHT-2(str), a spontaneous streptomycin resistant derivative of *Streptococcus mutans* strain BHT, was isolated according to the methods of Lederberg described in *J. Bacteriol.* 59: 211–215 (1950), using trypticase soy agar containing 1 mg/ml streptomycin sulfate as the selective medium.

Glucose tetrazolium plates were prepared according to Lederberg's methods [*J. Bacteriol.* 56: 695 (1948)], and contained 25.5 g antibiotic medium #2, 50 mg 1,3,5-triphenyl tetrazolium chloride, and 1% glucose (w/v) per liter of medium.

Strains of bacteria involved in this invention were maintained in 50% glycerol stabs at −20° C., and streaked on glucose tetrazolium medium weekly to check contamination and reversion and to serve as a source of inocula.

MUTAGENESIS

Exponentially growing cells of *Streptococcus mutans* strain BHT-2(str) cultured in Todd-Hewitt broth containing 0.5% glucose, were harvested by centrifugation and then washed twice in 0.1 M phosphate buffered saline (PBS, pH 7.0). These cells were then resuspended in PBS, pH 7.0, as before cultured, to a density of approximately $1.2 \times 10^8$ colony-forming units (c.f.u.) per ml.

0.015 ml of ethylmethane sulfonate was then added per ml of cell suspension and vortexed into solution, according to usual techniques. After 60 minutes incubation in a 37° C. water bath, mutagenesis was stopped by diluting the cell suspension with 9 volumes of PBS, pH 7.0. The cells were then harvested by centrifugation as before and resuspended in 10 ml of Todd-Hewitt broth containing 0.5% glucose. The culture was then grown to saturation overnight.

ISOLATION OF MUTANTS AND THEIR CHARACTERISTICS

*Streptococcus mutans* strain BHT-2(str) produces small white colonies when incubated in candle jars on glucose tetrazolium medium. After mutagenesis with ethylmethane sulfonate, however, as above described, a small number (ca. 1% frequency) of red mutant colonies were observed among the background of white, wild-type appearing colonies. These mutant colonies were isolated and purified by streaking on glucose tetrazolium medium.

Of the mutant strains isolated, those found useful in accordance with the invention, are characterized by their bright red color and larger colony size relative to the parent strain. The cells, moreover, are observed to be gram positive, spheroidal, and occur in pairs and chains. Other parameters that distinguish the desired mutant strains are the growth properties exhibited by the terminal pH attained by growing and non-growing cells of the strains, and the amount of lactic acid produced during fermentation of glucose. These results are tabulated below for a typically desired mutant.

| Strain | Terminal pH | Cell Yield (O.D. 580) | Lactic Acid (mM) |
|---|---|---|---|
| Parent | 3.82 | 2.4 | 49.8 |
| Mutant JH 140 | 4.30 | 2.4 | <1.0 |

Terminal pH was determined by subculturing strains (1:100) in Todd-Hewitt broth containing 1% glucose. After 48 hours incubation in candle jars at 37° C., the absorbance at 580 nm and pH of the cultures was determined. Lactic acid concentration of the subculture liquors was determined by gas-liquid chromatography. Salanitro, J. P. and P. A. Muirhead. 1975. Quantitative method for the gas chromatographic analysis of short-chain monocarboxylic and dicarboxylic acids in fermentation media. *Appl. Microbiol.* 29: 374–381.

As shown in the table, the mutant strain of the invention was significantly less effective in reducing the pH of the culture liquor than its parent. Cell yields for the various strains tested under these conditions were comparable. The apparent growth rates did not differ significantly, as has been previously reported. Hillman, J. D. 1977. Lactate Dehydrogenase Mutants of *Streptococcus mutans, J. Dent. Res.* 56: B88. The amount of lactic acid by the mutant strain during fermentation of glucose is seen from the table to be not detectable.

Similar differences in terminal pH attained were also observed when using limiting (0.2% w/v) glucose concentrations; and when washed, resting cell suspensions were incubated for 48 hours in fermentation buffer containing limiting or excess glucose. Yamada, T. and J. Carlsson. 1975. Regulation of Lactate Dehydrogenase and Change of Fermentation Products in Streptococci. *J. Bacteriol.* 124: 55–61.

The pH of cultures prepared as above, except that a different metabolizable carbon source is incorporated in the medium, is found to be higher than that of the parent strain. Those compounds found metabolized in addition to glucose include amygdalin, cellobiose, dextran, esculin, fructose, galactose, inulin, lactose, maltose, mannitol, mannose, melibiose, raffinose, ribose, salicin, sorbitol, sucrose, trehalose, and pyruvate. The following compounds did not cause a reduction in pH: adonitol, dulcitol glycerol, glycogen, inositol, melezitose, rhamnose, starch, xylose, lactate, lysine, formate, fumarate, and cysteine.

When mutants of the invention are incubated in the presence of sucrose, extracellular glucan is produced. The end products of glucose fermentation are significant amounts of formate and ethanol. Acetylmethyl carbinol is also present in considerable amounts; however, only a small amount of acetate is present. There is probably at least one other unidentified compound.

The work of Carlsson and co-workers and Brown and Patterson clearly indicate that *Streptococcus mutans* possesses one or more pathways alternate to lactic acid production for the dissimilation of pyruvate. Carlsson, J. and C. J. Griffith. 1974. Fermentation Products and Bacterial Yields in Glucose-Limited and Nitrogen-Limited Cultures of Streptococci. *Archs. oral Biol.* 19: 1105–1109; Yamada, T. and J. Carlsson. 1975. Regulation of Lactate Dehydrogenase and Change of Fermentation Products in Streptococci. *J. Bacteriol.* 124: 55–61; and Brown, A. T. and C. E. Patterson. 1973. Ethanol Production and Alcohol Dehydrogenase Activity in *Streptococcus mutans*. *Arch. oral Biol.* 18: 127–131. The other principal end-products which have been observed are formate, ethanol, and acetate, suggesting the probable existence of a phosphoroclastic (pyruvate formate-lyase) pathway. Carlsson, J. and C. J. Griffith, above.

OTHER MUTAGENS USEFUL IN THE PRACTICE OF THE INVENTION

LDH-deficient mutants which appear phenotypically similar to the mutagen-induced mutant JH140, can be obtained by use of mutagens such as ultraviolet light and nitrous acid. The technique for their use is described in a publication entitled *Experiments in Molecular Genetics* (1972), authored by Jeffrey Miller, Coldsprings Harbor Laboratory, Coldsprings Harbor, New York.

Although mutagens are preferred in the practice of the invention, the isolation on glucose tetrazolium of a spontaneous LDH-deficient mutant (ca. $10^{-5}$ frequency), which appears phenotypically similar to the ethylmethane sulfate-induced mutant, has also been accomplished.

ACID PRODUCTION BY RESTING CELLS.

One liter batch cultures of *Streptococcus mutans* strain BHT-2(str) and the mutant isolate JH140 were grown aerobically standing in Todd-Hewitt broth containing 0.5% glucose at 37° C. overnight. Cells were harvested by centrifugation at 4° C. and washed twice with 1 mM potassium phosphate buffer containing 50 mM KCl. The pellets were resuspended to a final volume of 100 ml in buffer, and stored at 4° C. until used.

Fermentation of glucose by the washed cell suspensions were carried out with constant rapid stirring in a 150 ml closed reaction vessel maintained at 37° C. by a circulating water jacket. The pH was maintained at the desired level, as indicated below, by a model 162 Automatic pH Controller (New Brunswick Scientific Co., New Brunswick, N.J.) with N NaOH serving as the titrant. After 30 min of temperature and pH equilibration, a 1 ml sample of cell suspension was removed as a zero time control. 0.2 ml of 1.2 N $H_2SO_4$ was added to this sample and vortexed before the addition of 0.01 ml of 20% (w/v) glucose. The fermentation was initiated by the addition of 1 ml of 20% glucose to the remaining 99 ml of cell suspension. The amount of titrant added was monitored at 1 min intervals, and at varying times 1 ml samples of the cell suspension were removed and added to vials containing 0.2 ml of 1.2 N $H_2SO_4$. The reaction was allowed to proceed until the rate of base consumption reached a plateau. The samples were stored frozen at $-20°$ C. until glucose concentrations could be determined (glucose oxidase method, Sigma Chemical Co.). Dry weights of the cell suspensions were measured as described by Carlsson (*J. Gen. Microbiol.*, 67: 69–76 (1971) and were between 5.4 and 6.5 mg/ml. The results are tabulated below.

|  | pH 7 | | pH 6 | | pH 5 | |
| --- | --- | --- | --- | --- | --- | --- |
|  | BHT-2 | MUTANT JH140 | BHT-2 | MUTANT JH140 | BHT-2 | MUTANT JH140 |
| N NaOH consumed (μmol/ml) | 20.0 ± .2 | 16.6 ± .8 | 20.0 ± .2 | 13.5 ± .8 | 14.8 ± .2 | 8.9 ± .2 |
| Glucose consumed (μmol/ml) | 10.4 ± .1 | 10.4 ± .1 | 9.9 ± .2 | 10.1 ± .1 | 10.2 ± .2 | 9.7 ± .0 |
| Acid produced: glucose consumed | 1.9 | 1.6 | 2.0 | 1.3 | 1.5 | 0.9 |

As shown in the table, the amount of glucose consumed in order to reach the plateau was approximately the same for both the parent and mutant strains at all pH values tested. However, the ratio of acid produced (measured as the amount of N NaOH consumed) to glucose consumed differed significantly between the strains. At pH 6 and 7, the data obtained for the parent strain approached the theoretical value of 2 for a homolactic fermentation. At pH 5, this value dropped somewhat, suggesting a (partial) shift to a less acidogenic pyruvate-degrading pathway.

The values for the mutant decreased significantly with each successive decrease in pH, and were ca. 80, 70, and 60% of the parental values at pH 7, 6, and 5, respectively. At pH 4.0 the reaction using the parental strain proceeded, but at a rate too slow for meaningful data to be obtained. At this pH the reaction using the mutant strain did not proceed, in agreement with the earlier finding that 4.3 was the terminal pH attained by a growing culture.

The rates of glucose consumption observed were always greater in the parent than in the mutant. In addition, it was noted that the rates of both acid production and glucose consumption by the parent showed hyperbolic kinetics, whereas the mutant displayed sigmoid kinetics.

ENZYME ASSAYS

Crude, cell-free extracts were prepared from 100 ml of the overnight cultures grown in Todd-Hewitt broth containing 0.5% glucose. The cells were harvested by centrifugation at 4° C. and resuspended in 1/50th volume of 0.05 M potassium phosphate buffer (pH 6.2) containing 0.02 M fructose 1,6-diphosphate. Cells were broken by one passage through a French press at 20,000 p.s.i. and cell debris was removed by centrifugation at 15,000 × g for 30 min. The resulting supernatants served as the crude extracts. Extracts were kept on ice and enzyme activities measured within 3 hours. The results are tabulated below.

| Strain | Enzyme (sp act; U/mg of protein)* | | | |
|---|---|---|---|---|
| | LDH | PGI | FDA | PK |
| Parent | .693 | .086 | .031 | .049 |
| Mutant | .011 | .166 | .072 | .109 |

*The assay for L(+) lactate dehydrogenase (LDH) activity was that described by Brown and Wittenberger (J. Bacteriol., 110:604–615 (1972). Phosphoglucose isomerase (PGI). Fraenkel, D. G. D. Kotlarz, and H. Buc. 1973. Two Fructose 6-Phosphate Kinase Activities in *Escherichia coli*. J. Biol. Chem., 248:4865–4866; fructose diphosphate aldolase (FDA). Maitra, P. K. and Z. Lobo 1971. A Kinetic Study of Glycolytic Enzyme Synthesis in Yeast. J. Biol. Chem., 246: 475–488; and pyruvate kinase (PK). Yamada, T. and J. Carlsson. 1975. Glucose-6-Phosphate-Dependent Pyruvate Kinase in *Streptococcus mutans*. J. Bacteriol., 124: 562–563. Protein was measured according to Lowry etal, using lyophilized bovine serum albumin as standard. Lowry, O. H., N. J. Rosebrough, A. L. Farr, and R. J. Randall. 1951. Protein Measurement With the Folin Phenol Reagent. J. Biol. Chem., 193: 265–275.

As seen from the table, cell free extracts of the mutant strain proved to have only ca 1% of parental levels of L(+)-LDH activity. Mixed wild-type and mutant extracts gave additive activities. Spectrophotometric assays of the other glycolytic enzymes revealed a 2–3 fold higher level of specific activities in the mutants compared to the parent in all of the strains tested.

GENETIC STUDIES

The nature of the genetic lesions in the mutants were analyzed by reversion studies. Following ethylmethane sulfonate mutagenesis, a culture of the JH140 was grown out overnight at 30° C. in Todd-Hewitt broth containing 0.5% glucose as earlier described. A sample of the culture was appropriately diluted, i.e. to about 500 c.f.u./ml. and spread on glucose tetrazolium plates. After 3 days incubation in candle jars at 30° C., wild-type appearing colonies were picked from among the background of red mutant colonies. After purification, single mutant colonies were replica-streaked onto glucose tetrazolium plates and incubated at 30° and 42° C. A number of isolates were obtained which showed a temperature-sensitive phenotype; i.e., they produced white colonies at 30° C. and red colonies at 42° C. A culture of one of those revertants was grown at 30° C. and crude, cell-free extracts prepared as before described, for enzyme assay, except that the assay was modified for heat lability studies. A sample of the extract containing 100–300 μg of protein was added to 1.1 ml of 0.05 M potassium phosphate buffer (pH 6.2), placed in a 55° C. water bath for varying times, chilled in ice, and returned to 25° C. Then 1.0 ml samples were assayed spectrophotometrically for remaining activity by the addition of 10.0 μmol sodium pyruvate, 0.1 μmol NADH and 20 μmol fructose 1,6-diphosphate; the rate of change in absorbance at 340 nm was recorded.

Untreated samples of extracts from the revertant contained 11.5% of the parental levels of L(+)-LDH activity. However, when samples of these extracts were pre-treated by heating in a water bath, a marked difference in enzyme thermolability was seen. Incubation for 9 min. at 55° C. destroyed only 10% of the enzyme activity present in extracts of the parent strain, whereas the identical treatment for 9 min., of an extract of the Mutant JH140 revertant destroyed over 90% of the LDH activity present.

Reversion studies, moreover, indicate that the observed phenotypes of the LDH-deficient mutants are due to single genetic lesions, believed to be point mutations in the structural gene for LDH. Screening of over 100 biochemical and physiological properties using the rapid identification system of Savitt et al. revealed no differences between parent and mutants, further confirming that a single gene defect is involved. Newman, M. G., S. S. Socransky, E. D. Savitt, M. Krichevsky, M. A. Listganten, and W. Lai. 1974. Characteristics of Bacteria Isolated From Periodontosis. J. Dent. Res. 53 Abstract 325, at p. 136.

The following examples which illustrate certain embodiments of the invention will aid in understanding thereof.

EXAMPLE 1

As an indication of the mutant's potential for competing with the wild-type parent strain in the oral cavity, their ability to adhere to hydroxyapatite and accumulate plaque in vitro was examined. The affinity of strain BHT-2(str) and the isolated mutant (JH140) to untreated and saliva-treated hydroxyapatite was determined.

Cultures of the strains tested were grown overnight in trypticase soy broth containing 0.2% glucose and 1 mCi/ml $^3$H-thymidine. Cells were harvested by centrifugation, washed twice in 1mM sodium phosphate buffer (pH 6.2) containing 50mM KCl, 1mM CaCl$_2$, and 0.1 mM MgCl$_2$, and resuspended in buffer to give 2.2 × 10$^7$ c.f.u./ml. 40 mg of washed spheroidal hydroxyapatite (BDH Biochemicals, Poole, England) were added to 1.5 ml of cell suspension and incubated for 1 hour at 25° C. with constant agitation. After 90 minutes, cells remaining unattached to hydroxyapatite were removed by repeated washing. The number of attached cells was determined by liquid scintillation counting of apatite samples, compared to controls. Saliva treatment entailed incubation of 40mg of apatite with 1.5 ml of heat-inactivated, clarified whole saliva for 24 hours at room temperature. The results are tabulated below:

|  | Untreated H.A. | | | Saliva-Treated H.A. | | |
| --- | --- | --- | --- | --- | --- | --- |
| Strain | No. of Attached Cells ± S.E. ($\times 10^6$) | % of Total Cells Attached | p* | No. of Attached Cells ± S.E. ($\times 10^6$) | % of Total Cells Attached | p* |
| Parent | 1.47 ± 0.03 | 7.3 ± 0.2 | — | 0.90 ± 0.04 | 4.6 ± 0.3 | — |
| JH140 | 2.14 ± 0.07 | 11.6 ± 0.5 | <.02 | 1.46 ± 0.02 | 8.1 ± 0.2 | <0.1 |

*T. test.

As shown in the table, when $2.2 \times 10^7$ washed cells in 1.5 ml of mM phosphate buffer were exposed to 40 mg of hydroxyapatite, significantly more mutant than wild-type cells become attached. The differences became more apparent, being some 2-fold, when the hydroxyapatite was first treated for 24 hours with clarified whole saliva.

Overnight cultures of the parent and mutant strain were subcultured 1:100 in Todd-Hewitt broth containing 5% sucrose. Sterile microscope slides were immersed aseptically in the cultures, and allowed to incubate for 24 hours in candle jars at 37° C. The slides were then removed and gently washed with distilled water to remove tenuously absorbed plaque. The differences observed were quite apparent; the mutant formed more plaque on the glass slide than did the parent strain.

EXAMPLE 2

This example shows that mutant strains of the invention are less virulent than the parent-strain.

Human tooth fragments were covered with parafilm wax leaving exposed a 6.2mm² enamel window. The fragments were suspended from wires to assist in their handling.

Overnight cultures were prepared of Streptococcus mutants strain BHT-2 and JH145 (phenotypically the same as mutant JH140 except for a lower frequency of reversion) in trypticase-soy broth containing 2% sucrose and 200 μgm/ml Streptomycin sulfate. These cultures were then subcultured 1:100 in the same media. The fragments were then immersed in these culture media and incubated at 37° C. anaerobically. At 24 hour intervals, the tooth fragments were gently transferred to fresh medium and reincubated.

After only ten days white spots characteristic of early dental caries were noticed beneath the plaque accumulated on the tooth fragments exposed to the Streptococcus mutans strains BHT-2(str). However, by comparison, even after 21 days exposure, the plaque accumulated by the tooth fragments exposed to the mutant isolate of the invention produced no apparent pathology.

EXAMPLE 3

This example demonstrates the in vivo cariogenicity of Streptococcus mutant strain BHT-2(str) and the mutant isolate (JH145) according to the invention in conventional rats.

Three Sprague-Dawley mother rats each with a litter of 12, three-day old pups were obtained from The Charles River Breeding Laboratories, Inc., Wilmington, MA. The animals were sustained on a vitamin fortified diet 2000, 54–56% sucrose, no fluoride, deionized water. Keyes, P. H. and H. V. Jordan. 1964. Periodontal Lesions In Syrian Hamsters. III Findings Related To An Infectuous and Transmissable Component. Archs, oral Biol. 9:377-400; Fitzgerald, R. J., H. V. Jordan, H. R. Stanley. 1960 Experimental Caries & Gingieal Pathogen Changes in Gnotobiotic Rats, J. Dent Res. 39:925-935.

At the pup ages of 6, 9, and 12 days, the mothers were each screened for Streptococcus mutans by swabbing the teeth and plating on Mitris salivarius agar (MS) and Mitris salivarius bacetracin (MSB) agar. Fecal samples were also obtained and suspended in 3 ml of 0.1M PBS (pH 7.0) and streaked out on MS and MSB plates. These tests proved negative; i.e., the mothers have no indigenous Strep. mutans. Accordingly, the pups also do not have Strep, mutans.

At the age of 21 days, the pups were weaned. They were then randomized into three groups of twelve.

Innoculums were prepared of the Strep. mutans strain BHT-2 (str) and the mutant isolate (JH145) by first growing up 10 ml. cultures in Todd-Hewitt broth containing 0.5% glucose to saturation. The cultures were centrifuged amd the cells were resuspended in 0.1M PBS (pH 7.0) to a concentration of about $10^{10}$ c.f.u./ml.

Accurate innoculum concentration was then determined, according to usual technique, by plating out $10^{-6}$ to $10^{-9}$ dilutions in PBS (pH 7.0)/glucose tetrazolium plates, after which they were incubated at 37° C. in candle jars for 48 hours. The results are indicated below:

|  | $10^{-6}$ | $10^{-7}$ | $10^{-8}$ | $10^{-9}$ |
| --- | --- | --- | --- | --- |
| BHT-2 | 268 | 55 | 2 | 0 |
| JH145 | 280 | 56 | 2 | 0 |

Initial innoculum was determined to be $3 \times 10^9$ cells/ml.

Using an Eppendorf pipet, and Group I of the twelve pups as the control group, 0.1 ml PBS (pH 7.0) was injected into the oral cavity of each rat. Group 2 and 3 rats were injected with innoculums BHT-2 and JH145 respectively.

The animals were reinjected with the respective cultures 4 days later by innoculums prepared as before described.

|  | $10^{-6}$ | $10^{-7}$ | $10^{-8}$ | $10^{-9}$ |
| --- | --- | --- | --- | --- |
| BHT-2 | 367 | 44 | 4 | 0 |
| JH145 | 263 | 22 | 1 | 0 |

The innoculums contained $4 \times 10^9$ cells/ml. and $3 \times 10^9$ cells/ml., respectively.

Fecal samples from each of the three groups were randomly collected, suspended in 3 mls. 0.1M PBS (pH 7.0) and streaked on glucose/tetrazolium streptomycin sulfate (1 mg/ml) to check for infection. These tests proved negative for Group I and positive for Groups 2 and 3.

After 14 weeks of infection, 7 of the animals from each group were sacrificed. These animals were decapitated, the heads defleshed and the maxillary and mandibular jaws of each animal separated according to usual techniques.

Three maxillary teeth (right) were removed from each rat's jaw and ground with 3 mls. PBS (pH 7.0) in a tissue grinder. Dilutions of $10^{-4}$, $10^{-5}$, $10^{-6}$ from each animal was plated out on glucose tetrozolium containing streptomycin sulfate. The plates were then incubated at 37° C. in candle jars for 48 hours, after which the colony count was determined in accordance with usual technique. The results are tabulated below:

| GROUP | CULTURE | ANIMAL# | $10^{-4}$ | $10^{-5}$ | $10^{-6}$ |
|---|---|---|---|---|---|
| #1 | PBS CONTROL | NO STREP MUTANS | | | |
| #2 | BHT-2 | 5 | 121 | 12 | 2 |
| " | " | 6 | ~400 | 38 | 5 |
| " | " | 7 | 286 | 28 | 3 |
| " | " | 8 | 167 | 12 | 2 |
| " | " | 9 | ~400 | 43 | 2 |
| " | " | 10 | 339 | 34 | 4 |
| " | " | 11 | 325 | 27 | 3 |
| #3 | JH145 | 5 | 132 | 13 | 1 |
| " | " | 6 | 7 | 2 | 0 |
| " | " | 7 | 210 | 18 | 2 |
| " | " | 8 | 109 | 7 | 1 |
| " | " | 9 | 66 | 5 | 0 |
| " | " | 10 | 130 | 11 | 1 |
| " | " | 11 | 46 | 4 | 0 |

The remaining jaws labeled as above indicated, were removed from the beetle colony in which they had been placed and suspended in 95% ethanol for 2 hours. The jaws were then removed, rinsed with d water and then suspended in 50/50 solution of ammonium hydroxide for ten days. The jaws were then removed, rinsed with deionized (d) water and immersed in xylene for 2 hrs. They were then prepared for scoring smooth surface caries by pressue air drying, after which the teeth were scored by the method described by P. H. Keyes *J. Dent. Res.* 37:1088–1099 (1958). The teeth were prepared for scoring deep fissure caries by first immersing them in a saturated solution of Nuclear Fast Red (small amount 10% Neutral Formalin to inhibit bacterial growth) for a period of 48 hours. The teeth were scored using 40x magnification. The maxillary and mandibular molars were hemisectioned in a mesiodistal sagittal plane freehand beneath a slow drip of water with a steel disc saw.

| MEAN, STANDARD DEVIATION & STANDARD ERROR TOTALS OF SULCAL, MORSAL, BUCCO-LINGUAL AND PROXIMAL LESIONS | | | | | |
|---|---|---|---|---|---|
| STRAIN | | SULCAL | MORSAL | BUCCO-LINGUAL | PROXIMAL |
| BHT-2 | MEAN | 79.57 | 1.86 | 45.42 | 0.286 |
|  | S.D. | 22.64 | 1.86 | 23.26 | 0.76 |
|  | S.E. | 8.56 | 0.70 | 8.79 | 0.29 |
| CONTROL | MEAN | 37.0 | 1.71 | 11.43 | 0.286 |
|  | S.D. | 10.92 | 2.14 | 10.32 | 0.49 |
|  | S.E. | 4.13 | 0.808 | 3.90 | 0.184 |
| JH145 | MEAN | 47.71 | 0.57 | 17.0 | 1.57 |
|  | S.D. | 22.47 | 0.97 | 8.60 | 1.10 |
|  | S.E. | 8.49 | 0.36 | 3.25 | 0.42 |

Statistical analysis (T-Test) of the above data showed a highly significant variance between the BHT-2 strains and either JH145 or the control (p<0.5%). The differences between JH145 and the control were not statistically significant. Thus, the cariogenic ability of the mutant to cause decay is comparable to the control. BHT-2 is highly cariogenic compared to the mutant and control.

EXAMPLE 4

This example demonstrates the in vivo cariogenicity of *Streptococcus mutans* strain BHT-2 (str), as compared to the JH145 mutant isolate, in germ free rats.

Nine germ free rats (Sprague-Dawley, Forsyth Dental Clinic, Boston, MA.) maintained in a germ free Reynier Isolator on diet 2000 (sterilized by gamma radiation, water sterilized by autoclaving) were infected by swabbing their mouths with a pure culture of the mutant isolate. The culture (5 mls) had been grown overnight in Todd-Hewitt broth (0.5% glucose), centrifuged and taken up in 0.1 M PBS (pH 7.0) to give a density of about $10^9$ colony-forming units per ml (c.f.u./ml). The cultures were placed in a sealed ampule, the outside of which was sterilized by spraying with 5% (w/v) peracetic acid before introduction into the isolator.

Random fecal samples were collected from three of the animals to insure infection, and check for contamination. The fecal samples were each suspended in 3 ml. PBS (pH 7.0) as before described, and streaked on glucose tetrozolium plates. The plates were then incubated at 37° C. for 48 hrs. in a candle jar. These tests proved negative for contamination and showed the rats to be infected.

After two weeks of infection, fecal sample quantitations were done on each animal. 5-10 mg. of fresh fecal sample from each animal was weighed out, transferred to a sterile tissue grinder and suspended in an equivalent amount of sterile 0.1M PBS (pH 7.0), i.e. 5 mg-5 ml. One ml. samples of dilutions $10^{-4}$ to $10^{-8}$ (initial dilution from T.G. = $10-^3$) were plated out on glucose tetrazolium plates, after which the plates were incubated at 37° C. for 48 hrs. in candle jars.

The colony count for fecal sample quantitations is tabulated below:

| ANIMAL | DILUTIONS | | | | |
|---|---|---|---|---|---|
|  | $10^{-4}$ | $10^{-5}$ | $10^{-6}$ | $10^{-7}$ | $10^{-8}$ |
| 1 | TMTC* | 223 | 11 | 1 | 0 |
| 2 | " | 70 | 10 | 2 | 0 |
| 3 | " | 210 | 21 | 15 | 0 |
| 4 | " | 250 | 27 | 13 | 0 |
| 5 | 143 | 9 | 0 | 0 | 0 |
| 6 | TMTC | 215 | 44 | 1 | 0 |
| 7 | 150 | 10 | 1 | 0 | 0 |
| 8 | TMTC | 24 | 6 | 1 | 0 |
| 9 | " | 72 | 4 | 2 | 0 |

*TMTC = Too many too count.

Ten germ free rats as above, maintained in a germ free isolator on diet 2000, were infected with a pure culture of BHT-2, this being obtained as above described.

Random fecal samples were collected and streaked as before to check for infection and contamination. The test proved negative for contamination and positive for infection.

After two weeks infection, fecal sample quantitation was done on each animal. The colony count for the $10^{-6}$ dilution is indicated below. Other dilutions were not prepared as this dilution proved satisfactory for colony count and was statically significant.

| Animal | 1 | 2 | 3 | 4 | 5 | 6 | 7 | 8 | 9 | 10 |
|---|---|---|---|---|---|---|---|---|---|---|
| Dilution ($10^{-6}$) | 140 | 153 | 87 | 78 | 102 | 65 | 85 | 145 | 106 | 250 |

After 8 weeks of infection 3 animals were sacrificed and the left maxillary molars extracted and ground in sterile tissue grinders with 3 ml 0.1M PBS, pH 7.0. The colony count on ground teeth in which the animals had been infected with the mutant isolate of the invention is tabulated below:

| | DILUTION | | |
|---|---|---|---|
| ANIMAL | $10^{-4}$ | $10^{-5}$ | $10^{-6}$ |
| 4 | 36 (28) | 4 (2) | 0 |
| 5 | 19 (44) | 1 (3) | 0 (1) |
| 6 | 67 (72) | 6 (7) | 0 |

( ) = no. of revertant colonies/plate.

The colony count on ground teeth from animals having been infected with *Streptococcus mutans* BHT-2 (str) is as follows:

| | DILUTION | | |
|---|---|---|---|
| ANIMAL | $10^{-4}$ | $10^{-5}$ | $10^{-6}$ |
| 5 | 177 | 22 | 4 |
| 7 | 166 | 26 | 7 |
| 8 | 188 | 21 | 3 |

After 14 weeks infection, five of the animals were sacrificed and the teeth were prepared for plating and scoring as earlier described.

The scores for these animals are as indicated below:

| STRAIN | | SULCAL | MORSAL | BUCCO-LINQUAL | PROXIMAL |
|---|---|---|---|---|---|
| | MEAN | 119.57 | 2.0 | 73.0 | 21.43 |
| BHT-2 | S.D. | 24.74 | 2.58 | 29.54 | 8.83 |
| | S.E. | 9.35 | 0.98 | 11.16 | 3.38 |
| | MEAN | 24.4 | 1.4 | 2.8 | 1.6 |
| JH145 | S.D. | 7.23 | 1.67 | 4.14 | 2.6 |
| | S.E. | 3.23 | 0.75 | 1.85 | 1.17 |

| T. TEST ON TOTAl CARIOUS LESIONS OF BHT-2 vs JH145 | | | | |
|---|---|---|---|---|
| STRAIN | MEAN | S.D. | S.E. | T-Test Value |
| BHT-2 | 216.00 | 40.82 | 15.43 | 9.19 sig.< 0.05% |
| JH145 | 30.2 | 7.09 | 3.17 | |

These results indicate a highly ($p<0.05\%$) significant-difference between BHT-2 and JH145 cariogenicity.

Unless otherwise specified, all reagents used in the practice of this invention were obtained from the Sigma Chemical Company, St. Louis, MO, and were the highest grade available. Auxiliary enzymes for spectrophotometric assays were obtained from Boehringer-Mannheim Corp., New York, NY.

As many different embodiments of this invention will now have occurred to those skilled in the art, it is to be understood that the specific embodiments of the invention as presented herein are intended by way of illustration only and are not limiting on the invention, but that the limitations thereon can be determined only from the appended claims.

What I claim is:

1. A method for controlling the incidence and severity of dental caries comprising injection into the oral cavity of a host susceptible to dental caries a dental-caries-controlling amount of a suitable innoculum of an effector strain for *Streptococcus mutans* BHT-2 (str).

2. A method for controlling the incidence and severity of dental caries which method comprises introducing into the oral cavity of a host susceptible to dental caries a dental-caries-inhibiting amount of an effector strain for the bacterium strain *Streptococcus mutans* wherein the effector strain is a mutant strain having the characteristics of bright red colonies when grown on glucose tetrazolium medium of relatively larger colony size than colonies of the parent strain grown on the same medium, spheroidal, gram positive cells occurring in pairs and chains and having a mutation in the structural gene for the enzyme, lactate dehydrogenase.

3. The method of claim 2 wherein the mutant strain isolated is characterized by a lack of detectable lactic acid when incubated in the presence of glucose.

4. The method of claim 2 wherein the mutant strain isolated is characterized by its relatively better adhesion to untreated and saliva-treated hydroxyapatite than said parent strain.

5. The method of claim 2 wherein the mutant strain isolated is characterized by its capacity to produce more plaque on glass slides and tooth enamel fragments than does the parent strain, when incubated in the presence of sucrose.

6. The method of claim 2 wherein the mutant strain isolated is characterized by its ability to metabolize a member from the group consisting of amygdalin, cellobiose, dextran, esculin, fructose, galactose, glucose, inulin, lactose, maltose, mannitol, mannose, melibiose, raffinose, ribose, salicin, sorbitol, sucrose, trehalose, and pyruvate, as evidenced by a relatively higher pH of cultures of the mutant strain compared to that of the parent strain when any of said members are incorporated in the culture medium of the parent strain and the mutant strain.

7. The method of claim 2 wherein the mutant strain is a biologically pure culture of the microorganism *Streptococcus mutans* strain BHT-2 (str) being capable of functioning as an effector strain for the parent strain in controlling the incidence and severity of dental caries.

8. The method of claim 2 wherein a suitable innoculum of an effector strain for *Streptococcus mutans* strain BHT-2 (str) is injected into the oral cavity of the host.

9. A method for controlling the incidence and severity of dental caries, which method comprises introducing into the oral cavity of a host susceptible to dental caries a dental-caries-inhibiting amount of an effector strain for the bacterium strain *Streptococcus mutans* wherein the effector strain is a mutant strain having the characteristics of:

(a) bright red colonies when grown on glucose tetrazolium medium of relatively larger colony size than colonies of the parent strain grown on the same medium, spheroidal, gram positive cells occurring in pairs and chains and having a mutation in the structural gene for the enzyme, lactate dehydrogenase;

(b) a lack of detectable lactic acid when incubated in the presence of glucose;

(c) relatively better adhesion to untreated and saliva-treated hydroxyapatite than said parent strain;

(d) its capacity to produce more plaque on glass slides and tooth enamel fragments than does the parent strain, when incubated in the presence of sucrose; and (e) its ability to metabolize a member from the group consisting of amygdalin, cellobiose, dextran, esculin, fructose, galactose, glucose, inulin, lactose, maltose, mannitol, mannose, melibiose, raffinose, ribose, salicin, sorbitol, sucrose, trehalose, and pyruvate, as evidence by a relatively higher pH of cultures of the mutant strain compared to that of the parent strain when any of said members are incorporated in the culture medium of the parent strain and the mutant strain.

10. A method for controlling the incidence and severity of dental caries, which method comprises introducing into the oral cavity of a host susceptible to dental caries a dental-caries-inhibiting amount of an effector strain for the bacterium strain *Streptococcus mutans* wherein the effector strain is a mutant strain identified as *Streptococcus mutans* JH140.

11. A method for controlling the incidence and severity of dental caries, which method comprises introducing into the oral cavity of a host susceptible to dental caries a dental-caries-inhibiting amount of an effector strain for the bacterium strain *Streptococcus mutans* wherein the effector strain is a mutant strain identified as *Streptococcus mutans* JH145.

* * * * *